(12) United States Patent
Wang et al.

(10) Patent No.: US 9,828,597 B2
(45) Date of Patent: Nov. 28, 2017

(54) BIOFUNCTIONAL MATERIALS

(75) Inventors: Ping Wang, Hudson, OH (US);
Minjuan Zhang, Ann Arbor, MI (US);
Hongfei Jia, Ann Arbor, MI (US);
Archana H. Trivedi, Mumbai (IN);
Masahiko Ishii, Okazaki (JP)

(73) Assignees: Toyota Motor Engineering & Manufacturing North America, Inc., Erlanger, KY (US); Toyota Motor Corporation, Toyota (JP); The University of Akron, Akron, OH (US)

( * ) Notice: Subject to any disclaimer, the term of this patent is extended or adjusted under 35 U.S.C. 154(b) by 1850 days.

(21) Appl. No.: 11/562,503

(22) Filed: Nov. 22, 2006

(65) Prior Publication Data
US 2008/0119381 A1    May 22, 2008

(51) Int. Cl.
| | |
|---|---|
| C09D 5/16 | (2006.01) |
| C12N 11/14 | (2006.01) |
| C09D 5/14 | (2006.01) |
| C12N 9/20 | (2006.01) |
| C12N 9/96 | (2006.01) |
| C12N 11/04 | (2006.01) |
| C12N 11/06 | (2006.01) |
| C12N 9/54 | (2006.01) |

(52) U.S. Cl.
CPC .............. *C12N 11/14* (2013.01); *C09D 5/14* (2013.01); *C09D 5/1637* (2013.01); *C09D 5/1687* (2013.01); *C12N 9/20* (2013.01); *C12N 9/54* (2013.01); *C12N 9/96* (2013.01); *C12N 11/04* (2013.01); *C12N 11/06* (2013.01); *C12Y 304/21062* (2013.01)

(58) Field of Classification Search
CPC ....................................................... C09D 5/16

USPC ............ 435/262, 264, 202, 243, 821, 262.5; 424/93.1, 94.1, 94.2
See application file for complete search history.

(56) References Cited

U.S. PATENT DOCUMENTS

| | | | |
|---|---|---|---|
| 3,220,928 A | 11/1965 | Brenner | |
| 3,705,938 A | 12/1972 | Seymour Hyman | |
| (Continued) | | | |

FOREIGN PATENT DOCUMENTS

| | | |
|---|---|---|
| AU | 2003304222 A1 | 1/2005 |
| AU | 2004257205 A1 | 1/2005 |
| (Continued) | | |

OTHER PUBLICATIONS

Drevon, Géraldine F., "Enzyme Immobilization into Polymers and Coatings", University of Pittsburgh School of Engineering Dissertation, Nov. 2002.

(Continued)

*Primary Examiner* — Gregory R Delcotto
*Assistant Examiner* — Preeti Kumar
(74) *Attorney, Agent, or Firm* — Dinsmore & Shohl LLP

(57) ABSTRACT

The present invention relates to compositions and a process in the field of self-cleaning system using digestive proteins. One composition includes a substrate, a digestive protein capable of decomposing a stain molecule, and a link moiety bound to both said digestive protein and said substrate. An alternative composition includes a digestive protein capable of decomposing a stain molecule and a coating substrate wherein said digestive protein may be dispersed in said coating substrate. The process claim includes binding a substrate to a surface and forming a linker moiety between a digestive protein and said substrate.

12 Claims, 7 Drawing Sheets

(56) References Cited

U.S. PATENT DOCUMENTS

| | | |
|---|---|---|
| 3,857,934 A | 12/1974 | Bernstein et al. |
| 4,016,043 A | 4/1977 | Schuurs et al. |
| 4,094,744 A | 6/1978 | Hartdegen et al. |
| 4,098,645 A | 7/1978 | Hartdegen et al. |
| 4,195,127 A | 3/1980 | Hartdegen et al. |
| 4,195,129 A | 3/1980 | Fukui et al. |
| 4,297,137 A | 10/1981 | Sachetto et al. |
| 4,552,813 A | 11/1985 | Grams |
| 4,910,234 A | 3/1990 | Yamamori et al. |
| 5,418,146 A | 5/1995 | Joo et al. |
| 5,559,163 A | 9/1996 | Dawson et al. |
| 5,770,188 A | 6/1998 | Hamade et al. |
| 5,868,720 A | 2/1999 | Van Antwerp |
| 5,912,408 A | 6/1999 | Trinh et al. |
| 5,914,367 A | 6/1999 | Dordick et al. |
| 5,919,689 A | 7/1999 | Selvig et al. |
| H1818 H | 11/1999 | Potgieter et al. |
| 5,998,200 A | 12/1999 | Bonaventura et al. |
| 6,030,933 A | 2/2000 | Herbots et al. |
| 6,150,146 A | 11/2000 | Hamade et al. |
| 6,291,582 B1 | 9/2001 | Dordick et al. |
| 6,342,386 B1 | 1/2002 | Powers et al. |
| 6,599,627 B2 | 7/2003 | Yeo et al. |
| 6,818,212 B2 | 11/2004 | Johansen et al. |
| 6,855,746 B2 | 2/2005 | Yoshitake et al. |
| 6,875,456 B2 | 4/2005 | Delest et al. |
| 6,881,711 B1 | 4/2005 | Gershun et al. |
| 6,905,733 B2 | 6/2005 | Russell et al. |
| 7,335,400 B2 | 2/2008 | Russell et al. |
| 7,632,793 B2 | 12/2009 | Lang |
| 7,932,230 B2 | 4/2011 | McDaniel |
| 7,939,500 B2 | 5/2011 | McDaniel |
| 8,388,904 B1 | 3/2013 | McDaniel et al. |
| 8,394,618 B2 | 3/2013 | Buthe et al. |
| 8,497,248 B2 | 7/2013 | McDaniel |
| 8,618,066 B1 | 12/2013 | McDaniel |
| 2003/0166237 A1 | 9/2003 | Allermann et al. |
| 2004/0009159 A1 | 1/2004 | Polsenski et al. |
| 2004/0063831 A1 | 4/2004 | Sheppard et al. |
| 2004/0109853 A1 | 6/2004 | McDaniel |
| 2004/0175407 A1 | 9/2004 | McDaniel |
| 2004/0241497 A1 | 12/2004 | Sasaki et al. |
| 2004/0259746 A1 | 12/2004 | Warren et al. |
| 2005/0049166 A1 | 3/2005 | Huang |
| 2005/0058689 A1 | 3/2005 | McDaniel |
| 2005/0059128 A1 | 3/2005 | Arnold et al. |
| 2005/0147579 A1 | 7/2005 | Schneider et al. |
| 2005/0176905 A1 | 8/2005 | Moon et al. |
| 2008/0038241 A1 | 2/2008 | Schasfoort et al. |
| 2008/0108745 A1 | 5/2008 | Russell et al. |
| 2008/0119381 A1 | 5/2008 | Wang et al. |
| 2009/0045056 A1 | 2/2009 | Berberich et al. |
| 2009/0238811 A1 | 9/2009 | McDaniel et al. |
| 2010/0210745 A1 | 8/2010 | McDaniel et al. |
| 2010/0248334 A1 | 9/2010 | McDaniel |
| 2010/0269731 A1 | 10/2010 | Tofte Jespersen et al. |
| 2010/0279376 A1 | 11/2010 | Wang et al. |
| 2011/0076738 A1 | 3/2011 | Wang et al. |
| 2011/0240064 A1 | 10/2011 | Wales et al. |
| 2011/0250626 A1 | 10/2011 | Williams et al. |
| 2012/0097194 A1 | 4/2012 | McDaniel et al. |
| 2012/0238005 A1 | 9/2012 | Wieland et al. |
| 2013/0065291 A1 | 3/2013 | Jia et al. |
| 2013/0137159 A1 | 5/2013 | Buthe et al. |

FOREIGN PATENT DOCUMENTS

| | | |
|---|---|---|
| CA | 2538124 A1 | 12/2004 |
| EP | 0670380 | 9/1995 |
| EP | 609691 B1 | 5/1998 |
| EP | 1161502 B1 | 12/2004 |
| EP | 1551927 A1 | 7/2005 |
| EP | 1609826 | 12/2005 |
| EP | 1644452 A2 | 4/2006 |
| EP | 1660596 A1 | 5/2006 |
| EP | 1661955 A1 | 5/2006 |
| FR | 2832145 A1 | 5/2003 |
| GB | 2410249 A | 7/2005 |
| GB | 2430436 A | 3/2007 |
| IL | 167413 A | 12/2010 |
| IL | 174122 A | 9/2011 |
| IL | 173658 A | 4/2012 |
| IL | 208769 A | 4/2012 |
| IL | 214668 A | 1/2013 |
| IL | 214669 A | 1/2013 |
| IL | 214670 A | 1/2013 |
| IL | 214671 A | 1/2013 |
| IL | 214672 A | 1/2013 |
| IL | 218129 A | 9/2013 |
| JP | 63202677 | 8/1988 |
| JP | 06192022 | 7/1994 |
| JP | 2002332739 A | 11/2002 |
| WO | 0050521 A1 | 8/2000 |
| WO | 0216521 A1 | 2/2002 |
| WO | 2005050521 A1 | 6/2005 |
| WO | WO-2005/103372 | 11/2005 |
| WO | 2009155115 A2 | 12/2009 |

OTHER PUBLICATIONS

Lt Col C. Carl Bostek, "Effective methods of in-line intravenous fluid warming at low to moderate infusion rates" Journal of the American Association of Nurse Anesthetists, vol. 60, No. 6, Dec. 1992.

Drevon, G. et al.; High-Activity Enzyme-Polyurethane Coatings, Biotechnology and Bioengineering, 79(7): 785-794, Sep. 30, 2002.

Jaroslava Turková; Immobilization of Enzymes on Hydroxyalkyl Methacrylate Gels; Immobilization Techniques; Methods in Enzymology; (1976); 344: pp. 66-83.

Johanna Mansfeld et al.; Site-specific and random immobilization of thermolysin-like proteases reflected in the thermal inactivation kinetics; Biotechnol. Appl. Biochem. (2000); pp. 189-195.

Kuniyo Inouye et al.; Engineering, expression, purification, and production of recombinant thermolysin; Biotechnology Annual Review; vol. 13; ISSN 1387-2656; pp. 43-64.

Mansfeld, et al.: The Stability of Engineered Thermostable Neutral Proteases from Bacillus Stearothermophilus in Organic Solvents and Detergents, Biotechnol. Bioeng. (2007) 97 (4): 672-679.

Masahiro Takagi et al.; Nucleotide Sequence and Promoter Region for the Neutral Protease Gene from Bacillus stearothermophilus; Journal of Bacteriology, Sep. 1985, pp. 824-831.

Minoru Kumakura et al.; 201. Interaction of Enzyme with Polymer Matrix in Immobilized Enzymes; Helvetica Chimica Acta; vol. 66; Fasc. 7; (1983); pp. 2044-2048.

Novic, S. et al.; Protein-containing hydrophobic coatings and films, Biomaterials, 23: 441-448, 2002.

U.S. Appl. No. 12/643,666, filed Dec. 21, 2009.

U.S. Appl. No. 14/093,347, filed Nov. 29, 2013.

U.S. Appl. No. 14/097,128, filed Dec. 4, 2013.

Wang P., et al.; Enzyme stabilization by covalent binding in nanoporous sol-gel glass for nonaqueous biocatalysis; Biotech, Bioeng. 2001, 74(3):249-255.

Physical Adsorption  Covalent Crosslinking

BIOFUNCTIONAL MATERIALS

BACKGROUND OF THE INVENTION

1. Field of the Invention

The present invention relates to self-cleaning compositions and a process for preventing and reducing surface stain accumulation due to bird droppings, bug wastes, food debris, and other stain causing materials.

2. Technical Background

Both interior and exterior surfaces of automobile, such as coatings, paints, and seat fabrics, are subject to contamination and corrosions when they are under prolonged exposure to bird dropping, insect debris, resins of conifer, microbes, gums, etc. Certain stains, such as insect-originated stains, are hard to remove with regular automatic brush-free washing. Interior surfaces and coatings may also be easily get stained with oil, protein, sugar and other ingredients in foods and beverages, and timely removal of such stains may present certain challenges.

Here, the present invention specifically involves the incorporation of digestive proteins including lysozymes, proteases, lipases, cellulases, etc., onto surfaces such as paints and coatings. The catalytic activity of the digestive proteins enables ongoing self-cleaning to reduce and eliminate stain contaminations. The mechanism of action of these digestive proteins is mainly enzymatic in nature and does not involve the use of any corrosive or oxidative components; therefore, they are environmentally friendly.

Stains of interests in the initial stage of this work include those formed from broken bodies of bugs, animal (like bird) wastes, foods, milk and other beverages, and cosmetic and personal care products. Although the detailed components vary with sources of stains, the major components of stains that are adhesive to surfaces are proteins, polysaccharides, fats or oils.

3. Description of Related Art

It is known to incorporate enzymes into coating or into substrates for the purpose of providing a surface with antimicrobial, antifungal or antifouling properties. Yet it is novel to the best knowledge of Applicants to attach digestive proteins to a surface for the purpose of enzymatically decomposing stain molecules in contact with the surface.

U.S. Pat. No. 6,818,212 discloses an enzymatic antimicrobial ingredient for disinfection and for killing microbial cells.

Wang et al. 2001 discloses lifespan extension of an enzyme upon its covalent binding at wet conditions; yet the reference does not seem to mention the utilization of such covalently bound enzyme in the area of surface self-cleaning.

U.S. Pat. No. 3,705,398 discloses polymeric articles having active antibacterial, antifungal and combinations of antibacterial and antifungal properties. The antibacterial and antifungal activating agents are distributed within the polymeric composition and migrate to the surface.

U.S. Pat. No. 5,914,367 discloses a method of preparing a polymer-protein composite including polymerizing a monomer in the presence of a protein dissolved in an organic phase via the ion-pairing of the protein with a surfactant. This reference, however, does not seem to mention the prevention or reduction of stain accumulation using the digestive power of such a polymer-protein composite.

U.S. Pat. No. 6,150,146 discloses a method of releasing a compound having antimicrobial activity from a matrix at a controlled rate. The method includes an enzyme and a substrate within the matrix beforehand to allow the enzyme and substrate to react with each other in the matrix, thereby to produce a compound having antimicrobial activity. The patent also discloses a coating composition comprising a film-forming resin, an enzyme, a substrate and any enzyme capable of reacting with the substrate.

U.S. 2005/0058689 discloses paints and coatings having antifungal growth and antibacterial materials. Specific chemicals and formations are disclosed for incorporation into painted surfaces which are antifungal compositions to inhibit growth of mold, bacterial, and fungi on building materials.

The object of the present invention is to provide self-cleaning composition and process containing digestive proteins for preventing and reducing stain accumulation.

SUMMARY OF THE INVENTION

The present invention provides, in a first aspect, a composition comprising a substrate, a digestive protein capable of decomposing a stain molecule, and a linker moiety.

The composition of the invention may be useful as a mechanism to prevent the accumulation of contacting stains and dirt by an "automatic" enzymatic degradation reaction. The digestive proteins of the composition may include proteases which hydrolyze protein molecules, lipases which hydrolyze lipids and fats, cellulases which hydrolyze cellulose, and amylases which hydrolyze carbohydrates, etc. It is neither required nor necessary for the digestive proteins to have their functional binding pockets all facing towards stain particles. A layer of digestive proteins delivers enough coverage and digesting activity even though the digestive proteins may be randomly arranged on a surface.

In a preferred embodiment of the invention, a surface may be pretreated with a layer of polymer comprising one or more active groups. A digestive protein suspension may be spin coated onto the polymer layer with the active groups to form covalent bonds between the proteins and the polymer layer. The active groups may comprise alcohol, thiol, aldehyde, carboxylic acid, anhydride, epoxy, and ester, etc. Alternatively, digestive proteins may be attached to nanoparticles before their suspension with paints or coatings.

The invention may be further directed to: a composition comprising a digestive protein for decomposing a stain molecule, and a coating substrate wherein the digestive protein is entrapped in the coating substrate. In this composition, the digestive protein may be selected from lysozymes, proteases, lipases, cellulases, glycosidases, amylases, etc.

In another aspect of the invention, a process is disclosed for reducing and or eliminating stain contaminations. The process comprises binding a substrate to a surface and forming a linker moiety between an active group of a digestive protein and the substrate. In this process, said substrate may comprise surface functional groups such as alcohol, thiol, aldehyde, carboxylic acid, anhydride, epoxy, ester, or any combination thereof.

BRIEF DESCRIPTION OF DRAWINGS

The present invention is further illustrated by reference to the accompanying drawings, in which.

DETAILED DESCRIPTION OF THE INVENTION

Figure 1:
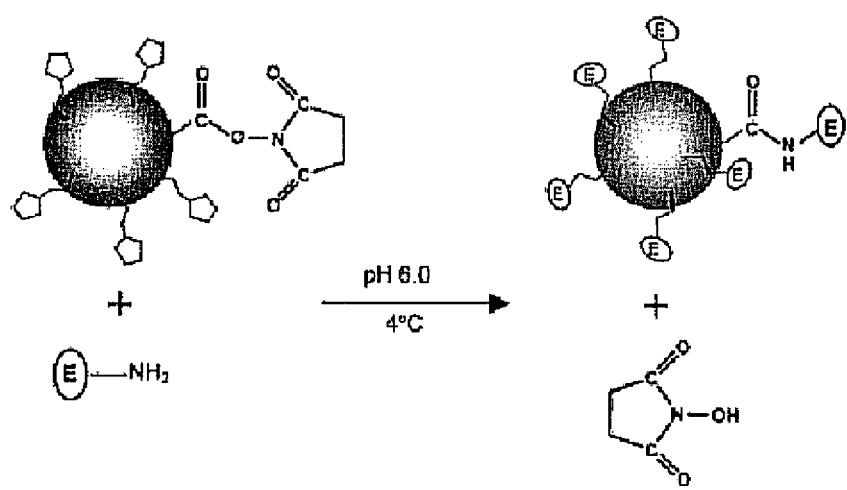
FIG. 1 is a depiction of an attachment of enzymes to the surface of polymeric nanoparticles.

The present invention relates to, in a first aspect, a composition comprising a substrate, a digestive protein capable of decomposing a stain molecule, and a linker moiety.

The present invention specifically involves the incorporation of one or more digestive proteins including lysozymes, proteases, lipases, cellulases, etc., onto surfaces such as paints and coatings. The catalytic activity of the digestive proteins enables ongoing self-cleaning to reduce and eliminate stain contaminations.

Various stains include those formed from broken bodies of bugs, animal (such as bird) wastes, foods, milk and other beverages, and cosmetic and personal care products. Although the detailed components vary with sources of stains, the major components of stains that are adhesive to surfaces are proteins, polysaccharides, fats or oils.

The activity of the digestive proteins toward different stain sources is evaluated in a solution environment. Tests are conducted at different conditions including different pH and temperature, in an attempt to evaluate the proteins' performance in an automobile environment instead of that in a washer machine as they have been traditionally applied. Tests include protein-related activity; starch-related activity tests; tests with oily stains. Protein activity unit is defined as: one unit of digestive protein hydrolyzes casein to produce absorbance difference equivalent to 1.0 µmol of tyrosine per minute at 37° C. under the conditions of the assay. Results of activity assay show covalent cross-linked protease present an activity that is nine times more than that of a physically absorbed protease.

There are several ways to incorporate the digestive proteins onto a substrate. One of which involves the application of covalent bonds. Specifically, free amine groups of the digestive proteins may be covalently bound to an active group of the substrate. Such active groups include alcohol, thiol, aldehyde, carboxylic acid, anhydride, epoxy, ester, or any combination thereof. This method of incorporating digestive proteins delivers unique advantages. First, the covalent bonds tether the proteins permanently to the substrate and thus place them as an integral part of the final composition with much less, if not at all, leakage of digestive protein species. Second, the covalent bonds provide for extended enzyme lifetime. Over time, proteins typically lose activity because of the unfolding of their polypeptide chains. Chemical binding such as covalent bonding effectively restricts such unfolding, and thus improves the protein life. The life of a protein is typically determined by comparing the amount of activity reduction of a protein that is free or being physically adsorbed with that of a protein covalently-immobilized over a period of time. Results have shown that a protein that is in free form or being physically adsorbed to a substrate loses its activity much faster that a protein in covalent-bond form.

Alternatively, digestive proteins may be uniformly dispersed throughout the substrate network to create a homogenous protein platform. In so doing, digestive proteins may be first modified with polymerizable groups. The modified proteins may be solubilized into organic solvents in the presence of surfactant, and thus engage the subsequent polymerization with monomers such as methyl methacrylate (MMA) or styrene in the organic solution. The resulted composition includes digestive protein molecules homogeneously dispersed throughout the network.

Also, digestive proteins may be attached to surfaces of a substrate in comparison to the above mentioned cross-linking methods. An attachment of digestive proteins corresponding to ~100% surface coverage was achieved with polystyrene particles with diameters range form 100 to 1000 nm.

The digestive proteins of the composition may include proteases which hydrolyze protein molecules, lipases which hydrolyze lipids and fats, cellulases which hydrolyze cellulose, and amylases which hydrolyze carbohydrates. It is neither required nor necessary for the digestive proteins to have their functional binding pockets all facing toward stain particles. A layer of digestive proteins delivers enough coverage and digesting activity even though the digestive proteins may be randomly arranged on a surface.

In a preferred embodiment of the invention, a surface is pretreated with a layer of polymer comprising one or more surface active groups of succinimide ester. A digestive protein suspension is spin coated onto the layer of the polymer with the active groups to form covalent bonds with the proteins. Alternatively, digestive proteins may be attached to nanoparticles before their suspension with paints or coatings.

The invention is further directed to a composition comprising a digestive protein capable of decomposing a stain molecule, and a coating substrate wherein the digestive protein may be entrapped in the coating substrate. In this composition, the digestive protein may be selected from lysozymes, proteases, lipases, cellulases, glycosidases, and amylases.

In another aspect of the invention, a process is disclosed for reducing and or eliminating stain contaminations. The process comprises binding a substrate to a surface and forming a linker moiety between an active group of a digestive protein and the substrate. In this process, the substrate may comprise surface active groups such as alcohol, thiol, aldehyde, carboxylic acid, anhydride, epoxy, ester, and any combinations thereof.

Example 1

Enzymes may be attached to surfaces of plastics. An enzyme attachment corresponding to ~100% surface coverage may be achieved with polystyrene particles with diameters range from 100 to 1000 nm. By coating with digestive protein, these particles may be used along with paints or coatings to functionalize the surfaces of materials. The same chemical bonding approach may be applied to coat enzymes onto preformed plastic parts, and thus form a protein coating on the parts' surfaces. As shown in FIG. 1, particles with diameters ranging from 100 nm to 1000 nm may be synthesized by emulsion polymerization. Emulsion polymerization is a type of polymerization that takes place in an emulsion typically incorporating water, monomer, and surfactant. The most common type of emulsion polymerization is an oil-in-water emulsion, in which droplets of monomer (the oil) are emulsified (with surfactants) in a continuous phase of water.

Particles as previously described may be synthesized by mixing an aqueous solution (mixture of water and ethanol, ~20 ml), containing a polymerizable surfactant (2-sulfoethylmethacrylate), a stabilizer (polyvinylpyrrolidone, PVP) and an initiator (2,2'-Azobis [2-methyl-N-(2-hydroxyethyl) propionamide]), will be mixed with an organic solution (~1 ml) of styrene, N-acryloxysuccinimide (NAS, a functionalized vinyl monomer), and divinyl benzene (~1% v/v). The particle size may be controlled by adjusting phase ratio (1/30~1/15, oil/aqueous) and the concentration of ethanol (0.125~0.50 ml/ml), 2-sulfoethyl methacrylate and PVP (0~5.5 mg/ml). The reaction may be performed with stirring at 70° C. for 10 h, followed by washing the resulted particles with ethanol and DI water in a stirred ultrafiltration cell with a polyethersulfone membrane (cut off MW: 300 kDa).

Example 2

Stains may be generated from different sources of contacts. Body residues of bugs, animal wastes, food, milk and other beverages, and cosmetic and personal care products may all cause stains. Although the detailed components vary with sources of stains, the major components that are adhesive to surfaces are proteins, simple sugars and polysaccharides, fats and/or oils. Digestive proteins including lipases, proteases, amylase and cellulose, each of them attacks different components, are thus far the most effective, safe and economic agents to fight against such stains. As shown below in Table 1, these proteins were examined and tested in our initial screening tests, and eventually we selected protease to proceed for the majority of the subsequent experiments due to the easiness in activity measurement.

TABLE 1

| Enzyme | Targeting Stains | Source | Functions | Standard testing conditions |
|---|---|---|---|---|
| Proteases | Bugs, dairy products, animal wastes | *Bacillus licheniformis* (Subtilisin Carlsberg) | Hydrolysis of protenaceious materials | Casein with Folin & Ciocalteu's Phenol dye, pH 7.5, 37° C., absorbance at 660 nm |
| Lipase AK | Fats and oils, cosmetics, inks | *Pseudomonas fluorescens* | Hydrolysis of oils and fats | p-nitro phenyl valerate, pH 7.7, 40° C., absorbance at 405 nm |
| □-Amylase | Juices, soft drinks, foods, animal wastes | *Bacillus subtilis* | Hydrolysis of starch | Dyed Starch, pH 6.9, 25° C., absorbance at 540 nm |
| Cellulase | Beverages, foods, animal wastes, | *Aspergillus niger* | Hydrolysis of cellulose | Dyed cellulose, pH 6 50° C., absorbance at 590 nm |

Example 3

Preparation of Enzyme Coating

N-acryloxy succinimide (392 mg), 1.2 ml of styrene and 29.2 mg of 4,4'-azobis-(4-cyanovaleric acid) were mixed with 16 ml of chloroform in a 20 ml glass reaction vial. The vial was purged with nitrogen, sealed and incubated at 70° C. for 12 hrs with stirring, followed by the removal of solvent by purging nitrogen. The polymer product was re-dissolved in chloroform at a concentration of 50 mg/ml. One milliliter of the resulting solution was spin-coated onto a polystyrene plate (11 cm in diameter) at 6000 rpm. Protease from Subtilisin Carlsberg was dissolved in 0.05 M phosphate buffer at a concentration of 10 mg/ml. The enzyme was applied onto the active polymer coated plate via 3-step layer-by-layer spin coating: 1) 1 ml of the protease solution, 2) 1 ml of protease solution containing 0.5% (V/V) of glutaraldehyde, 3) 1 ml of protease solution. The spin-coated plates were kept at 4° C. for 12 h, followed by extensive washing with 0.05 M Tris buffer (pH 8), 2M NaCl solution and DI water. Finally the plates were air-dried and cut into small pieces (1×2 cm). This method was designated as covalent cross-linking. As a comparison, similar procedure was applied on a polystyrene plate without the active polymer coating, which was called as physical adsorption.

Example 4

Visualization of Enzyme Coating

Figure 2:
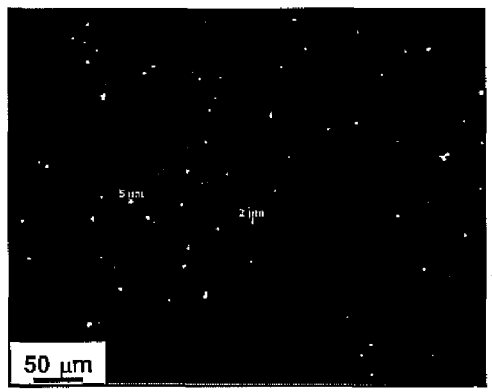
FIG. 2 is a depiction of fluorescence images of protease coating prepared via adsorption and covalent cross-linking.
Figure 2:
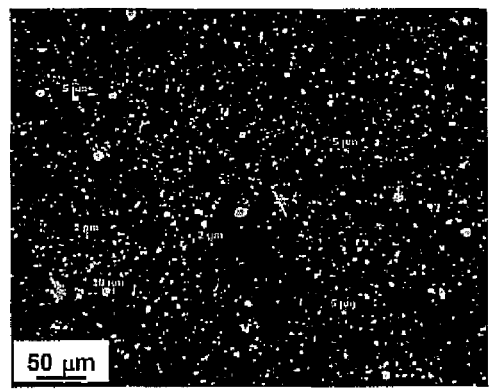

Fluorescent dye (Oregon green, Invitrogen Corp.) was first dissolved in dimethyl sulfoxide at a concentration of 2 mg/ml. The sample plates with physical adsorbed and covalently immobilized enzyme were incubated in the dye solution at room temperature with gentle shaking for 2 hours, followed by rinsing with DI water. The plates were then dried in nitrogen and observed under a fluorescence microscope. The images are shown in FIG. 2, where green color denotes the area covered with enzyme. Compared with physical adsorption, much more enzyme was immobilized on the surface using covalent cross-linking method.

Example 5

Determination of Enzyme Loading

Figure 3:
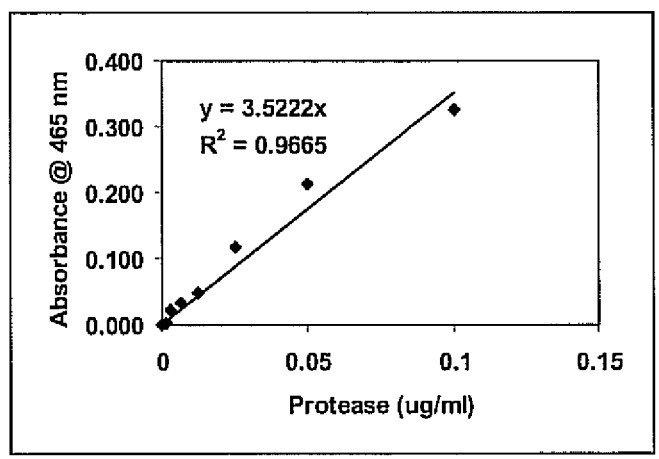
FIG. 3 shows a protein assay calibration curve.

The amount of enzyme attached to the plastic plate was determined by a reversed Bradford method. Typically, a working solution was first prepared by diluting Bradford reagent with DI water (1:5, by volume). A calibration curve was first obtained using free protease as the standards. In a 1 ml cuvette, 0.5 ml of protease solution was mixed with 0.5 ml of the working solution and then allowed to react for 5 min. The absorbance of the solution was measured at 465 nm on a spectrophotometer. After testing a series of different protease concentrations, a calibration curve was obtained as shown in FIG. 3.

To determine the loading of immobilized enzyme, a piece of enzyme-coated plate (1 cm×2 cm) was placed into a 20-ml glass vial, followed by the addition of 0.5 ml of DI water and 0.5 ml of the working solution. The vial was slightly agitated for 5 min at room temperature to allow binding of the dye to the immobilized enzyme. The absorbance of the supernatants was then recorded at 465 nm.

Similarly a blank plastic plate without enzyme coating was also measured as the control. The reading obtained with the blank plate was subtracted from the reading obtained from the enzyme loaded plate. Comparing the obtained reading difference with the calibration curve gave the loading on the plate, which was then normalized into a unit of □g/cm². The enzyme loading by covalent cross-linking and physical adsorption were 8.5 and 1.0 □g/cm², respectively.

Example 6

Verification of the Proteolytic Activity of Enzyme Coating

Enzyme in solution: The proteolytic activity of protease was determined using 0.65% (w/v) casein as the substrate. Protease solution (0.1 ml) was incubated with 0.5 ml of casein solution for 10 min at 37° C. The reaction was stopped by the addition of 0.5 ml of tricholoroacetic acid (110 mM). The mixture was centrifuged to remove the precipitation. The resulting supernatant (0.4 ml) was mixed with 1 ml of sodium carbonate (0.5 M) and 0.2 ml of diluted Folin & Ciocalteu's phenol reagent (1:4 by diluting Folin & Ciocalteu's phenol reagent with DI water), followed by incubation at 37° C. for 30 min. Finally the mixture was centrifuged again and the absorbance of the supernatant was measured at 660 nm on a spectrophotometer. Blank experiment was performed without enzyme solution by adding 100 µl of buffer and carrying out similar test. The absorbance of the blank was subtracted from the sample (enzyme solution).

Figure 4:
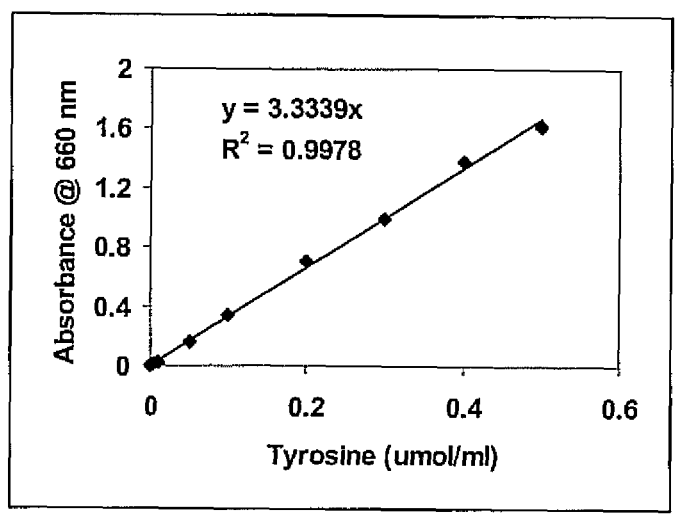
FIG. 4 shows a calibration curve for tyrosine (product of hydrolysis).

The activity unit was defined as: one unit of enzyme hydrolyzes casein to produce absorbance difference equivalent to 1.0 µmol of tyrosine per minute at 37° C. under the conditions of the assay. Tyrosine amino acid was used for calibration. Various concentrations of tyrosine were reacted with Folin-Ciocalteau reagent and the resulting calibration curve is shown in FIG. 4.

Enzyme coating: The activity of the immobilized protease was determined in a similar manner by using an enzyme coated polymer piece (1×2 cm) instead of enzyme in solution and a blank polymer coated piece as control. The activity of protein was termed as surface activity per unit area.

Results of activity assay showed that plates with covalent cross-linked protease afford $5.6 \times 10^{-3}$ unit/cm², while physical adsorbed enzyme only displayed an activity of $0.6 \times 10^{-3}$ unit/cm².

Example 7

Stain Degradation on Enzyme Coating

Figure 5:
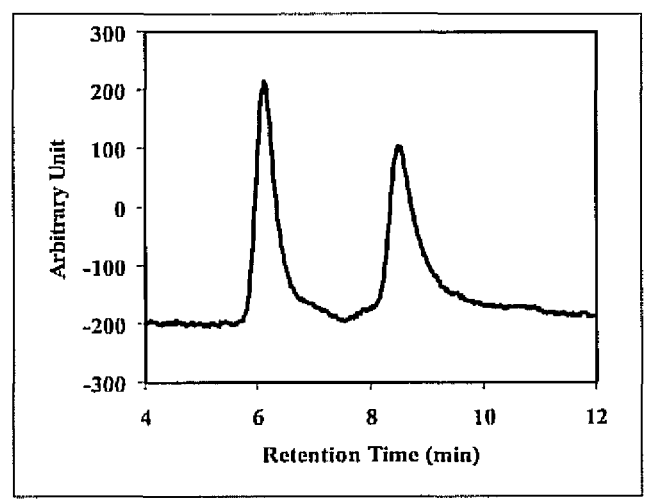
FIG. 5 shows a representative GPC chromatograph indicating egg white stain degradation.
Figure 6:
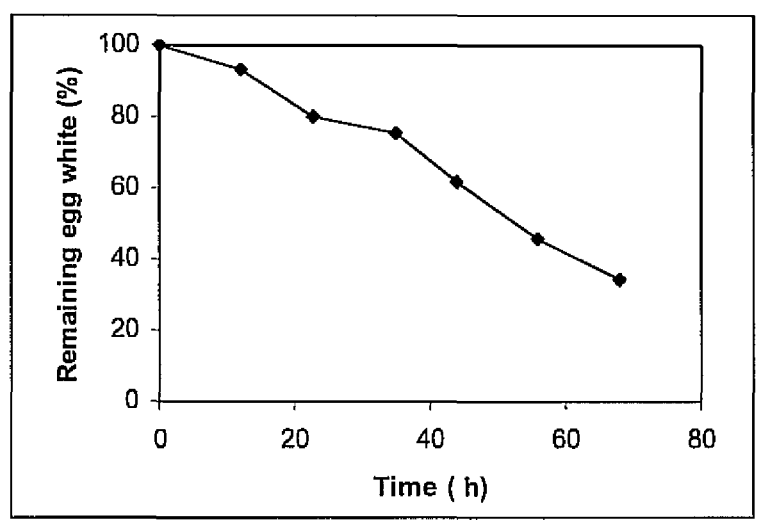
FIG. 6 shows the time course of egg white stain degradation.
Figure 7:
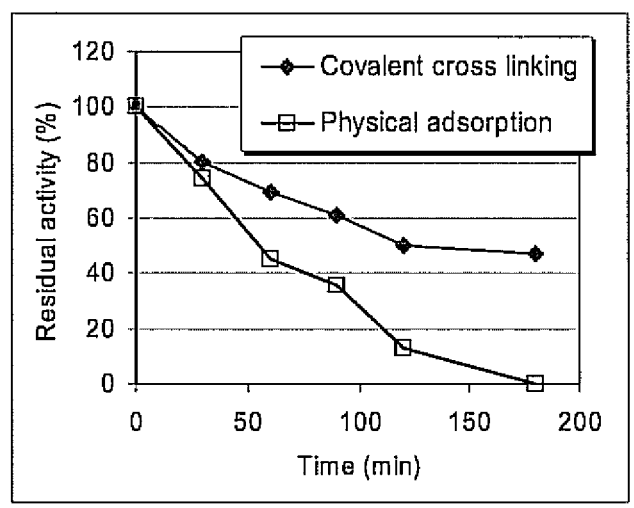
FIG. 7 shows thermal stability of protease coating at 80° C.

Egg white was used as the model stain to determine the stain degradation on enzyme coating. Onto a plate (11 cm in diameter) with protease-coating, 2 ml of egg white solution (10 mg/ml in DI water) was spin-coated at 2000 rpm. The plate was then cut into smaller pieces (1×2 cm) and kept at room temperature (25° C.) for various period of time to allow the degradation of egg white. After certain intervals, one small plate was carefully washed with DI water and the egg white in the washing solution was analyzed using gel permeation chromatography (GPC) to determine the molecular weight changes. Typically two peaks were found in the GPC chromatograph (FIG. 5): one has shorter retention time and the other has longer retention time, corresponding to the egg white and degradation products, respectively. Based on the area of the egg white peaks, a time course of egg white degradation was obtained as shown in FIG. 6. Control experiments were also performed using plates without protease coating, but no clear product peaks were identified.

Example 8

Thermal Stability of the Enzyme Coating

Thermal stability of the enzyme coating was studied at 80° C. in an air-heating oven. At certain time intervals, the sample plate(s) were taken out of the oven and the activity were measured following the procedure as described in Working Example 2. The decrease of activity with time was plotted in FIG. 9. It appeared that covalent cross-linked enzyme afforded better stability against thermal inactivation, as compared to physical adsorbed enzyme.

The inventions are not restricted to the illustrative examples described above. The examples are not intended as a limitation on the scope of inventions. Methods, apparatus, compositions and the like described herein are exemplary and not intended as a limitation on the scope of the inventions. Changes therein and other uses will occur to those skilled in the art. The scope of the inventions is defined by the scope of the claims.

The invention claimed is:

1. A composition for removing stains from a solid surface comprising:
   a digestive protein capable of decomposing stain forming molecules,
   a substrate applied to the solid surface, and
   a linker moiety bound to an outer surface of said substrate and an active group of said digestive protein, said linker moiety between said protein and said substrate and covalently linking said protein to a surface of said substrate,
   said digestive protein forming a layer on a surface of said substrate such that the digestive protein is surface exposed for reaction with a stain.

2. The composition according to claim 1, wherein the digestive protein comprises lysozymes, proteases, lipases, cellulases, glycosidases, amylases.

3. The composition according to claim 1, wherein said stain forming molecules are selected from the group consisting of proteins, oils, fats, and carbohydrates.

4. The composition according to claim 1, wherein said substrate comprises one or more surface active groups selected from alcohol, thiol, aldehyde, carboxylic acid, anhydride, epoxy, and ester.

5. The composition according to claim 1, wherein a decomposition product of said stain molecule decomposed by said digestive protein is removable by water-rinsing.

6. The composition according to claim 1, wherein said substrate comprises paint, and polymers.

7. A process for self-cleaning, comprising:
   binding a substrate to a surface; and
   forming a linker moiety between an active group of a digestive protein and said substrate so as to form the composition of claim 1.

8. The process according to claim 7, wherein said substrate comprises one or more selected from the group consisting of alcohol, thiol, aldehyde, carboxylic acid, anhydride, epoxy, and ester.

9. The process according to claim 7, wherein said surface is selected from the group consisting of metal, glass, paint, plastic, and fabrics.

10. The process according to claim 7, wherein said active group is selected from the group consisting of alcohol, amine, thiol, and carboxylic acid.

11. The process of claim 7, wherein the degradation of a stain molecule by said digestive protein occurs in a dry environment.

12. The process of claim 11, wherein the end product of said degradation is removable by water or rain.

* * * * *

UNITED STATES PATENT AND TRADEMARK OFFICE
CERTIFICATE OF CORRECTION

PATENT NO. : 9,828,597 B2
APPLICATION NO. : 11/562503
DATED : November 28, 2017
INVENTOR(S) : Ping Wang et al.

Page 1 of 1

It is certified that error appears in the above-identified patent and that said Letters Patent is hereby corrected as shown below:

In the Specification

In Column 4, Line 13, delete "form" and insert --from--, therefor.

Signed and Sealed this
Twentieth Day of March, 2018

Andrei Iancu
*Director of the United States Patent and Trademark Office*